(12) United States Patent
Xu

(10) Patent No.: US 12,286,461 B2
(45) Date of Patent: Apr. 29, 2025

(54) RECOMBINANT FUSED POLYPEPTIDE AND USE THEREOF

(71) Applicant: NANJING ANJI BIOLOGICAL TECHNOLOGY CO., LTD., Nanjing (CN)

(72) Inventor: Hanmei Xu, Nanjing (CN)

(73) Assignee: NANJING ANJI BIOLOGICAL TECHNOLOGY CO., LTD., Nanjing (CN)

( * ) Notice: Subject to any disclaimer, the term of this patent is extended or adjusted under 35 U.S.C. 154(b) by 733 days.

(21) Appl. No.: 17/635,952

(22) PCT Filed: Oct. 26, 2020

(86) PCT No.: PCT/CN2020/123551
§ 371 (c)(1),
(2) Date: Feb. 16, 2022

(87) PCT Pub. No.: WO2021/037289
PCT Pub. Date: Mar. 4, 2021

(65) Prior Publication Data
US 2022/0289801 A1    Sep. 15, 2022

(30) Foreign Application Priority Data
Aug. 27, 2019    (CN) .......................... 201910795102.X

(51) Int. Cl.
| | | |
|---|---|---|
| *C07K 14/47* | (2006.01) |
| *A61K 38/00* | (2006.01) |
| *A61K 38/16* | (2006.01) |
| *A61P 1/16* | (2006.01) |
| *A61P 9/00* | (2006.01) |
| *A61P 11/00* | (2006.01) |
| *A61P 13/12* | (2006.01) |
| *A61P 17/00* | (2006.01) |
| *A61P 31/04* | (2006.01) |
| *A61P 31/10* | (2006.01) |
| *A61P 31/12* | (2006.01) |
| *A61P 33/02* | (2006.01) |
| *C07K 14/00* | (2006.01) |
| *C07K 19/00* | (2006.01) |

(52) U.S. Cl.
CPC ................ *C07K 14/47* (2013.01); *A61P 1/16* (2018.01); *A61P 9/00* (2018.01); *A61P 11/00* (2018.01); *A61P 13/12* (2018.01); *A61P 17/00* (2018.01); *C07K 2319/00* (2013.01)

(58) Field of Classification Search
None
See application file for complete search history.

(56) References Cited

FOREIGN PATENT DOCUMENTS

| CN | 1328569 A | 12/2001 |
|---|---|---|
| CN | 105713095 A | 6/2016 |
| CN | 110511285 A | 11/2019 |

*Primary Examiner* — Suzanne M Noakes
*Assistant Examiner* — Jae W Lee

(57) ABSTRACT

The present invention discloses a recombinant fused polypeptide, a preparation method therefor, and use thereof. The recombinant fused polypeptide is represented by the following general formula: X-linker1-Y; Y-linker1-X; X-linker2-Y; Y-linker2-X, where X is PRCWRGEGGGGIVR-RADRAAVPGGGGRGD; and Y is Acetyl-SDKPGGGGT-SLDASIIWAMMQNGGGGLSKL. The recombinant fused polypeptide according to the present invention can treat various fibrosis diseases and symptoms, and therapeutic use includes anti-pulmonary fibrosis, anti-hepatic fibrosis, anti-skin fibrosis, anti-renal fibrosis, anti-myocardial fibrosis, and resistance to lung tissue lesions.

9 Claims, 6 Drawing Sheets

Specification includes a Sequence Listing.

RECOMBINANT FUSED POLYPEPTIDE AND USE THEREOF

TECHNICAL FIELD

The present invention relates to the field of biopharmaceuticals, and in particular, to a recombinant fused polypeptide and use thereof.

BACKGROUND

Tissue fibrosis is a disease that causes a decrease in parenchymal cells of organs and tissues and an increase in fibrillar connective tissues. Continuous progression of the disease may lead to structural damage and hypofunction of organs, and eventually failure, which seriously threatens health of patients. Worldwide, fibrosis of tissues and organs is the main cause of disability and death in many diseases.

In the process of tissue fibrosis, fibroblasts and myofibroblasts are key effector cells of tissue fibrosis. These effector cells can release a large number of collagen components, such as type I and type III collagen, which constitute ECM. A variety of cytokines are also involved in the process of fibrosis, and the most critical one is transforming growth factor-β (TGF-β). TGF-β is a multifunctional cell growth factor that regulates cell proliferation and differentiation. It can stimulate the proliferation of a large number of myofibroblasts and the excessive synthesis of ECM through directly stimulating the activation of in situ fibroblasts or through endothelial-mesenchymal transition (EnMT) and epithelial-mesenchymal transition (EMT) processes. When TGF-β is continuously activated due to damage, MAPK, EGF, and Wnt/β-catenin signals are cross-activated, leading to the progression of fibrosis. In addition to TGF-β, the regulation over a platelet-derived growth factor (PDGF), a basic fibroblast growth factor (BFGF), a connective tissue growth factor (CTGF), an insulin-like growth factor (IGF), angiogenesis-related cytokines, integrin, matrix metalloproteinase (MMP) and an inhibitor (TIMP) thereof, renin angiotensin-related protein, natriuretic peptide, and the like also affect occurrence of fibrosis.

The recombinant fused polypeptide designed according to the present invention has multiple targets, and has effects of an MMP inhibitor and inhibition of angiogenesis and integrin and the like. MMP inhibitor starts with MMP/TIMP, a key cytokine that regulates ECM and lung injury. An angiogenesis inhibitor can inhibit the release of cytokines such as TGF-β1 and VGFE. As the integrin can bind to TGF-β and promote the activation of TGF-β to release cytokine TGF-β1, inhibiting the integrin can inhibit the release of TGF-β1 and can inhibit the proliferation and activation of fibroblasts, and the inhibitor can act on the treatment of pulmonary fibrosis from the main pathogenesis in pathology. Polypeptides X and Y are polypeptides aiming at different targets. After being linked by Linker and recombinantly expressed, the polypeptides X and Y have activity of multiple targets and play a better therapeutic role. In addition, they can reduce the dosage and frequency of drug administration and improve the compliance and tolerance of patients to treatment.

1. Pulmonary Fibrosis

Pulmonary fibrosis (PF) is a serious pulmonary interstitial disease caused by many factors, and features the formation of pulmonary fibroblast foci and excessive accumulation of ECM. In view of similar pathological responses and disease characteristics of lung tissues after injury, pulmonary fibrosis is clinically commonly referred to as interstitial lung disease (ILD). Diffuse parenchymal lung disease, alveolar inflammation and interstitial fibrosis are basic pathological lesions of the ILD. Some disease causes are clear, while some disease causes are unknown. If the disease causes are unclear, the disease is referred to as idiopathic pulmonary fibrosis (IPF). Idiopathic pulmonary fibrosis has the highest incidence among pulmonary fibrosis, mostly in elderly men, with a median survival time of 3 years, and is the focus of current research.

Pulmonary fibrosis is a process of excessive repair of lung tissue. Wilson pointed out that when a problem occurs to any one or more links in an "injury-inflammation-repair" chain, the occurrence of fibrosis is caused. At present, the occurrence of pulmonary fibrosis may be attributed to the following three stages: (1) Injury stage: Alveolar epithelial cells are damaged by the stimulation of gas, dust, infection (bacteria or virus), drugs, radiation damage and other factors; (2) Effect stage: Injury promotes the apoptosis of alveolar epithelial cells and leads to oxidative stress response. Inflammatory cells (macrophages, TB lymphocytes, neutrophils, and the like) recruited at an injury site and a large number of secreted transforming growth factor-β (TGF-β) stimulate the proliferation and differentiation of fibroblasts and promote the formation of lung fibroblast foci; (3) Fibrosis stage: The formation of fibroblast foci and excessive secretion of ECM lead to the gradual replacement of parenchymal cells of lung tissue by interstitial cells, so that lung tissues lose elasticity and the hardness increases, and finally physiological functions of lung tissues are lost, resulting in that a patient dies due to respiratory failure caused by fibrosis.

A plurality of kinds of cells, such as pulmonary epithelial cells, endothelial cells, pulmonary inflammatory cells (mainly macrophages), and pulmonary interstitial cells (fibroblasts and myofibroblasts), are involved in the occurrence of fibrosis, and the pulmonary interstitial cells are key effector cells for the occurrence of pulmonary fibrosis. In addition, cytokines secreted by cells, such as transforming growth factor-β (TGF-β), a platelet-derived growth factor (PDGF), a basic fibroblast growth factor (BFGF), a connective tissue growth factor (CTGF), an insulin-like growth factor (IGF), a vascular endothelial growth factor (VEGF), integrin, matrix metalloproteinase (MMP), and an inhibitor (TIMP) thereof, also have a profound impact on the occurrence of pulmonary fibrosis.

The most critical cytokine is TGF-β, which is a multifunctional cell growth factor that can regulate cell proliferation and differentiation. The proliferation of a large number of myofibroblasts and the excessive accumulation of the ECM can be stimulated by directly stimulating the activation of in situ fibroblasts or through endothelial-mesenchymal transition (EnMT) and epithelial-mesenchymal transition (EMT) processes. When TGF-β is continuously activated due to damage, MAPK, EGF, and Wnt/β-catenin signals are cross-activated, leading to the progression of fibrosis. PDGF, BFGF, and VEGF as growth factors can promote the proliferation and differentiation of lung fibroblasts, and affect the progression of pulmonary fibrosis. MMP/TIMP is a main regulator of ECM, and the contents of the two play a key role in the balance of ECM. These cytokines have a more or less influence on the proliferation and activation of lung fibroblasts and the formation of collagen, and therefore reasonable regulation of cytokine expression facilitates the treatment of pulmonary fibrosis.

The recombinant fused polypeptide designed according to the present invention has multiple targets, and has effects of an MMP inhibitor and inhibition of angiogenesis and integrin and the like. MMP inhibitor starts with MMP/TIMP, a key cytokine that regulates ECM and lung injury. An angiogenesis inhibitor can inhibit the release of cytokines such as TGF-β1 and VGFE. As the integrin can bind to TGF-β and promote the activation of TGF-β to release cytokine TGF-β1, inhibiting the integrin can inhibit the release of TGF-β1 and can inhibit the proliferation and activation of fibroblasts, and the inhibitor can act on the treatment of pulmonary fibrosis from the main pathogenesis in pathology.

2. Hepatic Fibrosis

As a pathological change caused by chronic liver damage resulting from a variety of reasons, hepatic fibrosis features excessive and abnormal deposition of extracellular matrix components in the liver, and affects the function of the liver. The hepatic fibrosis is a necessary stage for the development of chronic liver disease to cirrhosis. Factors that can cause almost all kinds of chronic liver diseases can cause hepatic fibrosis, and disease causes may roughly fall into infectious diseases, congenital metabolic defects, chemical toxicities, autoimmune liver diseases, and the like. Excessive deposition of extracellular matrix in the liver is a characteristic change of hepatic fibrosis. At present, it is believed that the activation of hepatic stellate cells (HSCs) is a central link of hepatic fibrosis. However, a mechanism of occurrence and progression of hepatic fibrosis is very complicated. At present, the research mainly focuses on the activation and transformation of hepatic stellate cells into myofibroblasts and fibroblasts. Possible ways are activation of a TGF-β signal transduction pathway, a PDGF receptor-mediated signal transduction pathway, a TNF-α-mediated signal transduction pathway, cyclooxygenase-2 (COX-2), diffuse ECM, angiogenesis, oxidative stress-mediated hepatic fibrosis, or the like.

Hepatic fibrosis is a necessary pathological stage for all kinds of chronic hepatitis to develop into cirrhosis, and is the manifestation of liver injury self-repair. According to WHO report, there are 20 million cases of hepatitis B virus infection in China, and hepatic fibrosis has occurred to most of these patients. Therefore, how to treat hepatic fibrosis has become an urgent problem to be resolved.

3. Renal Fibrosis

As the common pathway of almost all renal diseases to end-stage renal failure, renal fibrosis (including glomerular fibrosis, renal interstitial fibrosis, and renal vascular fibrosis) is one of the main pathological manifestations of various chronic renal diseases, and is the final outcome of various glomerular, vascular and tubulointerstitial diseases. Studies have shown that no matter what the cause of kidney disease is, the development of renal fibrosis is progressive, and glomerular fibrosis and renal interstitial fibrosis play an important role.

Due to stimulation by various pathogenic factors such as trauma, infection, inflammation, blood circulation disorder, and immune response, intrinsic cells of the kidney are damaged, and deposition and accumulation of a large amount of collagen occur when the disease progresses to a later stage, causing the renal parenchyma to gradually harden and form scars until the kidney completely loses organ functions. The process of fibrosis and hardening of intrinsic cells in the kidney is also the process of renal fibrosis. In the process of renal fibrosis, the infiltration of renal interstitial inflammatory cells, activation of fibroblasts and excessive deposition of extracellular matrix are all related to the abnormal expression of integrin. The basic pathological cause of renal fibrosis is the excessive activation of fibroblasts. Inhibiting the excessive activation of fibroblasts can effectively inhibit the development of renal fibrosis.

At present, most drugs for the treatment of renal fibrosis have problems such as high toxicity, low safety, and single pharmacological actions. The recombinant fused polypeptide according to the present invention is under a multi-target design and can inhibit renal fibrosis in multiple ways.

4. Skin Fibrosis

Skin fibrosis is excessive scar formation of skin and a result of pathological wound healing response. Skin wound healing includes several stages: hemostasis, inflammation, proliferation, and tissue maturation. The whole process is induced and regulated by a series of complex factors (such as growth factors and cytokines). Skin fibrosis can be driven by immune, autoimmune, and inflammatory mechanisms. The balance between collagen synthesis and degradation plays a key role in the pathological process of fibrosis. Some cytokines, such as TGF-β and interleukin-4 (IL-4), promote wound healing and fibrosis, while other cytokines, such as interferon-γ (IFN-γ) and tumor necrosis factor-α (TNF-α), resist fibrosis. Fibroblasts of normal skin are in a dormant state. After skin injury, fibroblasts begin to activate and massively proliferate, express α-smooth muscle actin (α-SMA), and synthesize a large number of connective tissue proteins.

The most common method used to treat skin fibrosis is immunosuppressive therapy. The basic principle is that autoimmune causes inflammation of diseases and subsequent tissue damage and fibrosis. Commonly used drugs include methotrexate, cyclophosphamide, and cyclosporin. Although some improvements in immunosuppressive therapy have been observed, concerns about the safety of the drugs and the lack of confirmed clinical data and demonstrable efficacy still exist. Therefore, there is an urgent clinical need to develop an effective pharmaceutical preparation for the treatment of skin fibrosis, fibrotic skin diseases and pathological scar formation of the skin.

5. Myocardial Fibrosis

Myocardial fibrosis is cardiac interstitial remodeling that features excessive proliferation of cardiac interstitial fibroblasts and excessive deposition and abnormal distribution of collagen. Pathologically, myocardial fibrosis mainly features increased collagen deposition, proportion imbalance of different kinds of collagen, and especially increased proportion and disordered arrangement of type I and type III collagen, accompanied by proliferation of myocardial fibroblasts. The synthesis and degradation of extracellular matrix are affected by multiple factors, and the balance between matrix metalloproteinase-9 (MMP-9) and tissue inhibitor-1 (TIMP-1) thereof is a main regulating factor in the degradation process. At present, increasing attention is paid to the role of MMP-9/TIMP-1 in myocardial fibrosis. Myocardial fibrosis is closely related to a variety of cardiovascular diseases, such as hypertension, chronic heart failure, and dilated cardiomyopathy, and is a potential risk factor of sudden cardiac death. At present, the specific pathogenesis of myocardial fibrosis is not very clear. It is mainly believed that myocardial fibrosis is closely related to a renin-angiotensin-aldosterone system, various cytokines, oxidative stress, and the like. These factors affect the occurrence and progression of myocardial fibrosis through the same or different conduction pathways.

At present, no marketed drug for treating myocardial fibrosis is available, and therefore there is an urgent clinical need to develop a drug for treating myocardial fibrosis.

SUMMARY

The Sequence Listing created on Mar. 29, 2022 with a file size of 5.00 KB, and filed herewith in ASCII text file format as the file entitled "Sequence_Listing-G204RAYT0001US.TXT," is hereby incorporated by reference in its entirety.

1. To-be-Resolved Problem

In view of the problems of existing polypeptides such as high chemical synthesis costs, many impurities and single targets, the present invention provides a recombinant fused polypeptide. In the recombinant fused polypeptide according to the present invention, a 293T cell culture expression method is used to link two polypeptides with different active targets instead of a chemical synthesis method, which reduce costs and impurities. The linkage increases effect targets and curative effect of the recombinant polypeptide. The linkage of the two polypeptides makes the recombinant polypeptide have respective targets of the two polypeptides, so that the recombinant fused polypeptide has multiple target active functions, and has good therapeutic effects in pulmonary fibrosis, hepatic fibrosis, renal fibrosis, myocardial fibrosis, skin fibrosis and lung tissue lesions. The recombinant fused polypeptide according to the present invention can target multiple targets and inhibit fibrosis in multiple ways.

2. Technical Solutions

To resolve the foregoing problems, technical solutions adopted by the present invention are as follows:

A recombinant fused polypeptide is provided, where the recombinant fused polypeptide is expressed by the following general formula:

X-linker1-Y; Y-linker1-X; X-linker2-Y; Y-linker2-X, where X is PRCWRGEGGGGIVRRADRAAVPGGG-GRGD (SEQ ID NO: 5); and
Y is Acetyl-SDKPGGGGTSLDASIIWAMMQNGGG-GLSKL (SEQ ID NO: 6).

In the recombinant fused polypeptide, linker1 is GGGGSGGGGSGGGGS (SEQ ID NO: 7); and linker2 is AEAAAKEAAAKEAAAKEAAAKK (SEQ ID NO: 8).

Specifically, a recombinant fused polypeptide has anti-fibrosis activity, and an amino acid sequence thereof is:

```
recombinant fused polypeptide I:
PRCWRGEGGGGIVRRADRAAVPGGGGRGD-linker1-

SDKPGGGGTSLDASIIWAMMQNGGGGLSKL:

recombinant fused polypeptide II:
Acetyl-SDKPGGGGTSLDASIIWAMMQNGGGGLSK

L-linker1-PRCWRGEGGGGIVRRADRAAVPGGGG

RGD;

recombinant fused polypeptide III:
PRCWRGEGGGGIVRRADRAAVPGGGGRGD-linker2-

SDKPGGGGTSLDASIIWAMMQNGGGGLSKL;

and
recombinant fused polypeptide IV:
Acetyl-SDKPGGGGTSLDASIIWAMMQNGGGGLSKLlinker2-PRCWRGEGGGGIVRRADRAAVPGGGGRGD.

Preferred sequences are as follows:
                                       (SEQ ID NO: 1)
PRCWRGEGGGGIVRRADRAAVPGGGGRGDGGGGSGGG

GSGGGGSSDKPGGGGTSLDASIIWAMMQNGGGGLSKL;

(SEQ ID NO: 2)
Acetyl-

SDKPGGGGTSLDASIIWAMMQNGGGGLSKLGGGGSGGG

GSGGGGSPRCWRGEGGGGIVRRADRAAVPGGGGRGD;

(SEQ ID NO: 3)
PRCWRGEGGGGIVRRADRAAVPGGGGRGDAEAAAKEAA

AKEAAAKEAAAKKSDKPGGGGTSLDASIIWAMMQNGGG

GLSKL;
and (SEQ ID NO: 4)
Acetyl-SDKPGGGGTSLDASIIWAMMQNGGGGLSKLA

EAAAKEAAAKEAAAKEAAAKKPRCWRGEGGGGIVRRAD

RAAVPGGGGRGD.
```

The polypeptide according to the present invention further includes a polypeptide sequence with 80% homology with the foregoing sequence.

Use of the above recombinant fused polypeptide in the preparation of anti-pulmonary fibrosis, anti-hepatic fibrosis, anti-renal fibrosis, anti-myocardial fibrosis and anti-skin fibrosis drugs and drugs for resisting lung tissue lesions is provided.

Preferably, the lung tissue lesions include bacterial pneumonia, viral pneumonia, mycoplasma pneumonia, fungal pneumonia, chlamydia pneumonia, and protozoal pneumonia.

The recombinant fused polypeptide according to the present invention has multiple targets, can target angiogenesis, integrins, matrix metalloproteinases, and the like, and can inhibit the process of fibrosis in many ways. The polypeptide reduces the activation of fibroblasts and the deposition of extracellular matrix, can slow down the fibrosis process, and can further inhibit the infection of various lung diseases.

3. Beneficial Effects

Compared with the prior art, the present invention has the following beneficial effects:

(1) Molecules of the recombinant fused polypeptide according to the present invention are linked by a flexible or rigid linker, and the polypeptides at two ends can vary and move, thereby having better ductility; and polypeptide X and polypeptide Y have different targets, which can inhibit the fibrosis process in many ways.

(2) In the recombinant fused polypeptide according to the present invention, two polypeptides are recombined and linked by a flexible or rigid linker, which increases the molecular weight of polypeptide molecules, prolongs the half-life of drugs, and enhances the stability and pharmaceutical effects.

(3) The recombinant fused polypeptide according to the present invention can be used for treating various fibrosis diseases, including pulmonary fibrosis, hepatic fibrosis, renal fibrosis, myocardial fibrosis, and skin fibrosis.

(4) In a pulmonary fibrosis model, the recombinant fused polypeptide according to the present invention can significantly reduce the expression of HYP and TGF-β1 in lung tissues, significantly improve a situation of pulmonary fibrosis, and prolong its life cycle.

(5) In a hepatic fibrosis model, the recombinant fused polypeptide according to the present invention can significantly reduce the expression of HYP in liver tissues and significantly improve a situation of hepatic fibrosis.

(6) In a renal fibrosis model, the recombinant fused polypeptide according to the present invention can significantly reduce the expression content of TGF-β1 in renal tissues and significantly improve a situation of renal fibrosis.

(7) In a myocardial fibrosis model, the recombinant fused polypeptide according to the present invention can significantly reduce the content of HYP in heart tissues and significantly improve a situation of myocardial fibrosis.

(8) In a skin fibrosis model, the recombinant fused polypeptide according to the present invention can significantly reduce the expression content of HYP in skin and significantly improve a situation of skin scar hyperplasia.

The recombinant fused polypeptide according to the present invention also has a good inhibitory effect on the infection of lung diseases, and the inhibitory rate is 78% or above.

Figure 1:
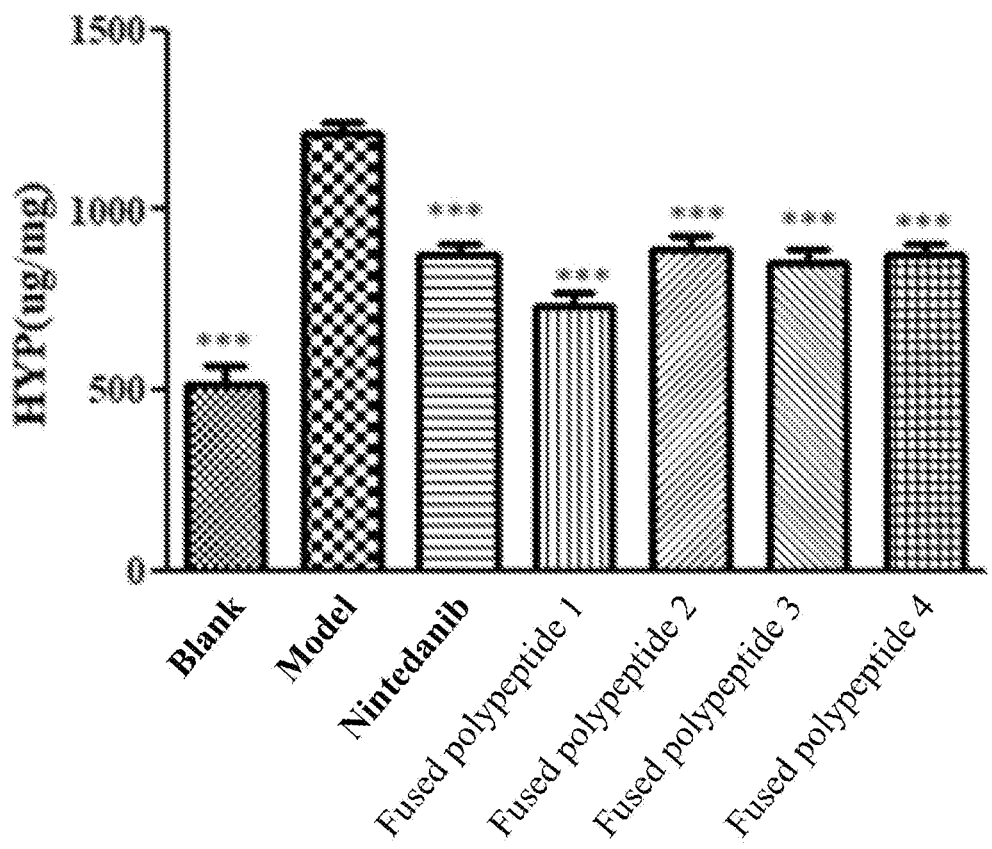
FIG. 1 is a diagram showing that recombinant fused polypeptides I, II, III and IV according to the present invention can lower the hydroxyproline content in a pulmonary fibrosis model.

Note: Fused polypeptides I, II, III and IV are fused polypeptides 1, 2, 3 and 4, the same below.

DETAILED DESCRIPTION

The present invention will be further described below with reference to specific examples.

Example 1 Preparation of Fused Polypeptides I, II, III and IV

```
Recombinant fused polypeptide I:
X-linker1-Y; an amino acid sequence is:
PRCWRGEGGGGIVRRADRAAVPGGGGRGD-linker1-Acetyl-

SDKPGGGGTSLDASIIWAMMQNGGGGLSKL;

recombinant fused polypeptide II:
Y-linker1-X; an amino acid sequence is:
Acetyl-SDKPGGGGTSLDASIIWAMMQNGGGGLSKL-linker1-

PRCWRGEGGGGIVRRADRAAVPGGGGRGD;

Recombinant fused polypeptide III:
X-linker2-Y; an amino acid sequence is:
PRCWRGEGGGGIVRRADRAAVPGGGGRGD-linker2-Acetyl-

SDKPGGGGTSLDASIIWAMMQNGGGGLSKL;

recombinant fused polypeptide IV:
Y-linker2-X;
and an amino acid sequence is:
Acetyl-SDKPGGGGTSLDASIIWAMMQNGGGGLSKL-Iinker2-

PRCWRGEGGGGIVRRADRAAVPGGGGRGD.

In the recombinant fused polypeptide,
linker1 is
GGGGSGGGGSGGGGS;
and linker2 is
AEAAAKEAAAKEAAAKEAAAKK.

Preferred sequences are as follows:
Fused polypeptide 1:
PRCWRGEGGGGIVRRADRAAVPGGGGRGDGGGGSGGGGSGGGGS

SDKPGGGGTSLDASIIWAMMQNGGGGLSKL;

fused polypeptide 2:
Acetyl-

SDKPGGGGTSLDASIIWAMMQNGGGGLSKLGGGGSGGGGSGGGG

SPRCWRGEGGGGIVRRADRAAVPGGGGRGD;

fused polypeptide 3:
PRCWRGEGGGG1VRRADRAAVPGGGGRGDAEAAAKEAAAKEAAA

KEAAAKKSDKPGGGGTSLDASIIWAMMQNGGGGLSKL;
and fused polypeptide 4:
Acetyl-SDKPGGGGTSLDASIIWAMMQNGGGGLSKLAEAAAKE

AAAKEAAAKEAAAKKPRCWRGEGGGGIVRRADRAAVPGGGGRGD.
```

The polypeptide according to the present invention further includes a polypeptide sequence with 80% homology with the foregoing sequence.

1. Construction of a Cloning Vector

Sangon Biotech (Shanghai) Co., Ltd. was entrusted to synthesize the DNA sequence of the foregoing recombinant fused polypeptide, which was connected to commercial expression vectors to form cloning vectors. The construction processes of the foregoing different recombinant fused polypeptide cloning vectors were consistent.

2. Expression of the Recombinant Fused Polypeptide

Transient transfection is one of the ways to introduce DNA into eukaryotic cells. In transient transfection, recombinant DNA is introduced into a highly infectious cell line to obtain transient high-level expression of a target gene.

Enough target protein samples can be obtained in a short time period for experimental research, which reduces the cell screening time required for stable transfection. A commercial Expi293 expression system or another suitable transient transfection expression system was used to express the foregoing recombinant fused polypeptide. The expression processes of the foregoing different recombinant fused polypeptides are the same. The experimental process was as follows.

2.1 Plasmid Preparation

A glycerol tube with a cloning vector preservation strain was taken from a refrigerator at −80° C., and put into a 2 L shake flask containing 500 mL Amp-resistant LB medium, and shake culture was performed overnight at 37° C. and 160 rpm. After the culture, 5000 g of strain was centrifuged for 5 min and thalli were collected, and plasmids were extracted by using a commercial plasmid extraction kit for endotoxin removal. The plasmid concentration was controlled to be 1 mg/mL or above, and then the plasmids were filtered and sterilized by using a sterile 0.22 μm microporous filter membrane to complete plasmid preparation.

2.2 Preparation for Transient Transfection 293F cells or other suitable mammalian cells used for transfection were passaged every four days from the day of resuscitation, and at least three passages were carried out before transient transfection. In the process of passage, the passage volume should be expanded as needed according to a final transfection medium volume.

2.3 Transient Transfection (30 mL Transfection Volume was Used as an Example, and Adjusted Several Times as Required)

(1) On the day before the experiment, $6*10^7$ cells were inoculated into 30 mL of Expi293 expression medium, and shake culture was performed at 37° C. and 125 rpm in the presence of 8% $CO_2$.

(2) On the day of the experiment, the cells cultured on the previous day were counted first, the cell density should be $(3-5)*10^6$ cells/mL, and the viability was greater than 95%.

(3) $7.5*10^7$ cells were transferred into a new 125 mL conical flask, and the preheated Expi293 expression medium was replenished to 25.5 mL.

(4) Preparation of a plasmid-transfection reagent mixture

① 30 μg of plasmid DNA was reconstituted in 1.5 mL of Opti-MEM I reduced serum medium and mixed slowly and evenly.

② 81 μL of ExpiFectamine 293 reagent was added to the Opti-MEM I reduced serum medium to a constant volume of 1.5 mL. The solution was gently and evenly mixed and incubated at room temperature for 5 min (long-time incubation would affect the conversion efficiency).

③ The two solutions were gently and evenly mixed, and incubated at room temperature for 20-30 min. Preparation of the plasmid-transfection reagent mixture was completed.

(5) 3 mL of plasmid-transfection reagent mixture was added to the cell culture solution in step (3).

(6) Shake culture was performed at 37° C. and 125 rpm for 20 hours in the presence of 8% $CO_2$.

(7) 150 μL of ExpiFectamine 293 transfection enhancer 1 and 1.5 mL of ExpiFectamine 293 transfection enhancer 2 were added.

(8) Shake culture was performed at 37° C. and 125 rpm in the presence of 8% $CO_2$. After culture for 6 days, the cell culture supernatant was collected for purification of the target protein.

3. Purification of the Recombinant Fused Polypeptide

An appropriate gel chromatography process was adopted for purification (such as cation exchange chromatography and/or anion exchange chromatography), purified samples were collected, and the purification processes of the foregoing recombinant fused polypeptides were the same.

Finally, a 10 kDa ultrafiltration membrane was used to concentrate the target protein to a concentration greater than 5 mg/L, and then the samples (fused polypeptides 1, 2, 3 and 4) were subpackaged and stored in a refrigerator at −80° C. Methods such as SDS-PAGE and HPLC were used to detect the purity of the samples, and were used for the evaluation of the druggability properties such as in vivo and in vitro activity evaluation.

Example 2 Pulmonary Fibrosis Animal Model

Experimental Animals and Materials:

1. Experimental Animals:

Source and strain: clean SD rats, provided by Comparative Medicine Center of Yangzhou University (laboratory animal production license: SCXK (Su) 2012-0004); Laboratory Animal Use License: SYXK (Su) 2012-0035).

Weight: 180-200 g at the time of purchase, 190-210 g at the beginning of modeling, and 180-200 g at the beginning of administration.

Gender: Male.

2. Experimental Materials:

| | |
|---|---|
| Bleomycin | Manufacturer: Han Hui Pharmaceutical Co., Ltd. |
| Normal saline | Manufacturer: Anhui Double Crane Pharmaceutical Co., Ltd. |
| Chloral hydrate | Manufacturer: Sinopharm Chemical Reagent Co., Ltd. |
| Rat TGF-β1 ELISA kit | Manufacturer: Tianjin Annuo Ruikang Biotechnology Co., Ltd. |
| Alkaline HYP kit | Manufacturer: Nanjing Jiancheng Bioengineering Institute |
| BIBF1120 (nintedanib) | Manufacturer: Jinan Synovel Chemical Co., Ltd. |

3. Experimental Method:

SD rats were anesthetized by intraperitoneal injection of 4% chloral hydrate with a concentration of 1 mL/100 g. After anesthesia, the rats were fixed and their necks were disinfected by using cotton with 75% alcohol. The skin of the rat neck was longitudinally cut with scissors, and the fascia and muscle were longitudinally bluntly torn with tweezers to expose the trachea. A syringe was inserted into the trachea to inject 5 mg/kg bleomycin, while a blank group was injected with an equal amount of normal saline. Then a rat plate was quickly erected and rotated, the rats' breathing was observed, the neck wound was sterilized after rotation and was sewn, and an amoxicillin anti-inflammatory drug was sprinkled on the suture. After the operation, the rats were put back into a dry and clean cage for resting, waiting for awakening. The rats were awakened after about 1-2 hours, and then fed normally. On the $7^{th}$ day after modeling, modeling group animals randomly fell into a model group, a Nintedanib positive drug group, recombinant fused polypeptide 1, 2, 3 and 4 dosage groups, and a normal control group, and the groups were administered separately for an administration cycle of 15 days. Living situations of rats were observed every day and their weights were weighed. After administration for 15 days, the eyeballs were removed and blood was taken, the rats were dissected, and lungs were taken. The content of TGF-β1 in serum and the content of HYP in lung tissues were detected.

4. Experimental Grouping and Dosage Setting

TABLE 1

Experimental grouping and dosage regimen

| Group | Drug | Dosage | Administration mode | Administration frequency | Quantity |
|---|---|---|---|---|---|
| Blank group | Normal saline | 0.5 mL/200 g | Subcutaneous injection | Once a day | 14 |
| Model group | Normal saline | 0.5 mL/200 g | Subcutaneous injection | Once a day | 14 |
| Positive drug | Nintedanib | 25 mg/kg | Intragastric administration | Once a day | 14 |
| Test drug (1) | Fused polypeptide 1 | 10 mg/kg | Subcutaneous injection | Once every five day | 14 |
| Test drug (2) | Fused polypeptide 2 | 10 mg/kg | Subcutaneous injection | Once every five day | 14 |
| Test drag (3) | Fused polypeptide 3 | 10 mg/kg | Subcutaneous injection | Once every five day | 14 |
| Test drug (4) | Fused polypeptide 4 | 10 mg/kg | Subcutaneous injection | Once every five day | 14 |

Note:
Fused polypeptides 1, 2, 3 and 4 are fused polypeptides I, II, III and IV, the same below.

5. Experimental Results (1) Impact of a Recombinant Fused Polypeptide on the Survival Rate of SD Rats Induced by Bleomycin As shown in Table 2, compared with the survival rate (50%) of SD rats in the model group, the survival rate of SD rats in each test drug group was higher than that of the model group, each test drug could significantly increase the survival rate of SD rats, and the survival rates of the fused polypeptide 1 group, the fused polypeptide 2 group and the fused polypeptide 3 group was equivalent to that of the positive drug group. The survival rate of the fused polypeptide 4 (92.9%) was higher than that of the positive drug group (85.7%).

TABLE 2

Impact of a recombinant fused polypeptide on survival rate (%) of SD rats with bleomycin-induced pulmonary fibrosis

| Group | Dosage (mg/kg) | Number of animals at the beginning | Number of animals at the end | Survival rate (%) |
|---|---|---|---|---|
| Blank group | — | 14 | 14 | 100 |
| Model group | — | 14 | 7 | 50 |
| Positive drug group | 10 | 14 | 12 | 85.7 |
| Fused polypeptide 1 | 10 | 14 | 12 | 85.7 |
| Fused polypeptide 2 | 10 | 14 | 12 | 85.7 |
| Fused polypeptide 3 | 10 | 14 | 12 | 85.7 |
| Fused polypeptide 4 | 10 | 14 | 13 | 92.9 |

Figure 2:
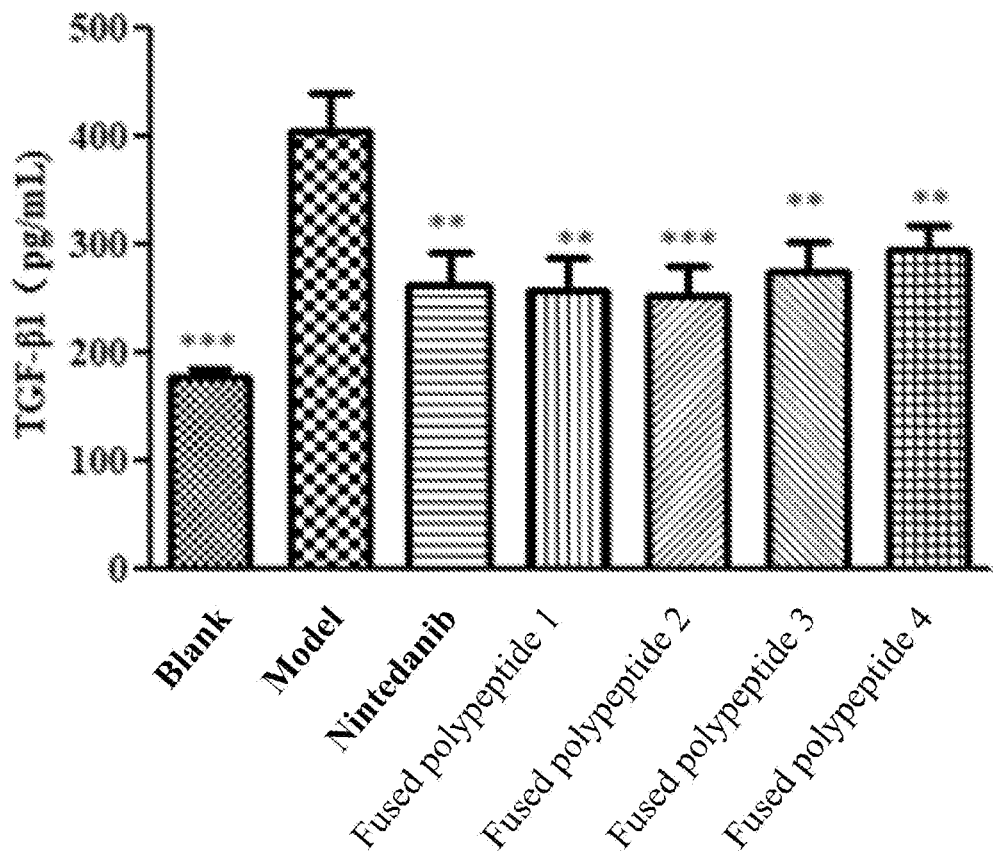
FIG. 2 is a diagram showing that recombinant fused polypeptides I, II, III and IV according to the present invention can lower the TGF-β1 content in the pulmonary fibrosis model.

(2) Impact of a Recombinant Fused Polypeptide on the Content of TGF-β1 in Serum of SD Rats with Bleomycin-Induced Pulmonary Fibrosis Lung tissues of each group were taken to detect the content of hydroxyproline in the lung tissue to obtain the results shown in FIG. 1. As the characteristic protein of collagen, hydroxyproline can reflect the content of collagen in the lung tissue from the side. TGF-β1 is the most important fibrogenic factor. In pulmonary fibrosis, the expression content of TGF-β1 was significantly increased. The result is shown in FIG. 2, and the blank group and the fused polypeptide 2 group were highly significant different from the model group (*P<0.001). After administration, all groups could significantly reduce the content of TGF-β1 in serum, the nintedanib positive drug group, the fused polypeptide 1 group and the fused polypeptide 3 group were highly significantly different from the model group (P<0.01), and the recombinant fused polypeptide 4 group was significantly different from the model group (*P<0.05).

Example 3 Hepatic Fibrosis Animal Model

1. Experimental Animals:
Source and strain: SPF level, SD rats, provided by Shanghai Xipuer-Bikai Experimental Animal Co., Ltd. (laboratory animal license: SCXK (hu) 2013-0016)
Weight: 180-200 g at the time of purchase and 200-220 g at the beginning of modeling
Gender: Male.

2. Experimental Materials:

| | |
|---|---|
| Carbon tetrachloride | Manufacturer: Shanghai Aladdin Reagent Co., Ltd. |
| Normal saline | Manufacturer: Anhui Double-Crane Pharmaceutical Co., Ltd. |
| Olive oil | Manufacturer: Sangon Biotech (Shanghai) Co., Ltd. |
| Alkaline HYP kit | Manufacturer: Nanjing Jiancheng Bioengineering Institute |
| Glutamic-oxalacetic transaminease test kit | Manufacturer: Nanjing Jiancheng Bioengineering Institute |
| Glutamic-pyruvic transaminase test kit | Manufacturer: Nanjing Jiancheng Bioengineering Institute |

3. Experimental Method

Male SD rats fell into the following groups, and the groups were shown in the following table. Modeling was performed on the rats. Each group other than the blank group was injected with 40% $CCl_4$ intraperitoneally twice a week, the first injection was performed at 3 mL/kg, and then injection was performed at 2 mL/kg. Modeling was performed for 8 weeks to induce hepatic fibrosis. After the intraperitoneal injection of $CCl_4$ for the fourth time, the drugs were administered according to Table 3. After induction for 8 weeks, the administration was stopped. The SD rats were dissected the next day, and blood was taken. The liver tissue was stored in a refrigerator at −80° C. for further use. The expression of HYP in the hepatic tissue of rats was detected.

4. Experimental Grouping and Dosage Regimen

TABLE 3

Experimental grouping and dosage regimen

| Group | Drug | Dosage | Administration mode | Administration frequency | Quantity |
|---|---|---|---|---|---|
| Blank group | Normal saline | 0.5 mL/200 g | Subcutaneous injection | Once a day | 11 |
| Model group | Normal saline | 0.5 mL/200 g | Subcutaneous injection | Once a day | 11 |
| Positive drug | Colchicine | 0.4 mg/kg | Intragastric administration | 5 times/week | 11 |
| Test drug (1) | Fused polypeptide 1 | 6 mg/kg | Subcutaneous injection | Once every five days | 11 |
| Test drug (2) | Fused polypeptide 2 | 6 mg/kg | Subcutaneous injection | Once every five days | 11 |
| Test drug (3) | Fused polypeptide 3 | 6 mg/kg | Subcutaneous injection | Once every five days | 11 |
| Test drug (4) | Fused polypeptide 4 | 6 mg/kg | Subcutaneous injection | Once every five days | 11 |

Figure 3:
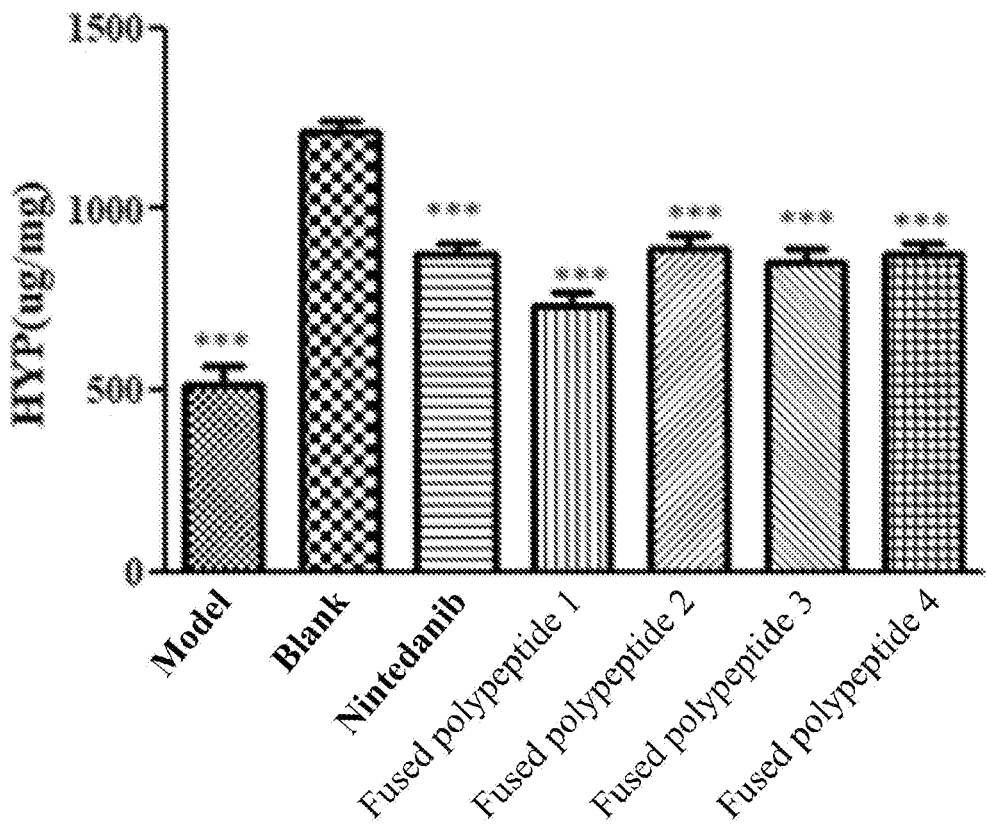
FIG. 3 is a diagram showing that recombinant fused polypeptides I, II, III and IV according to the present invention can lower the HYP content in a hepatic fibrosis model.

5. Experimental Results (1) Content of HYP in the Liver Tissue of Rats in Each Group Liver tissues of each group were taken to detect the content of hydroxyproline in the liver tissue to obtain the results shown in FIG. 3. As the characteristic protein of collagen, hydroxyproline can reflect the content of collagen in the liver tissue from the side. As shown in FIG. 3, the content of HYP in the model group was significantly higher than that in the blank group. Recombinant fused polypeptides 1, 2, 3 and 4 and nintedanib, the positive drug, could significantly lower the expression of HYP in liver tissue, and each polypeptide group and the positive drug group were highly significantly different from the model group (***$P<0.001$).

Example 4 Renal Fibrosis Animal Model

1. Experimental Animals

Clean grade male SD rats, purchased from Nanjing Qinglong Mountain Animal Farm, and weighed 180-200 g at the time of purchase, 190-210 g at the beginning of modeling, and 180-200 g at the beginning of administration.

2. Experimental Materials:

| | |
|---|---|
| Normal saline | Manufacturer: Anhui Double-Crane Pharmaceutical Co., Ltd. |
| Rat TGF-$\beta$1 ELISA kit | Manufacturer: Tianjin Annuo Ruikang Biotechnology Co., Ltd. |
| Alkaline HYP kit | Manufacturer: Nanjing Jiancheng Bioengineering Institute |

3. Experimental Method

A renal fibrosis animal model was established. SD rats were anesthetized with 4% chloral hydrate, injected with 1 mL/100 g intraperitoneally, fixed to an operation board, and sterilized in an operation area for further use. The abdominal cavity was cut open about 3-4 mm to the left of the ventrimeson, left kidney ureter was separated in an operation group, the ureter was ligated and separated close to the ureter near the lower pole of the inferior pole of kidney, and the ureter was cut short between two ligations after the double ligations. Muscular layers and abdominal walls were sewed layer by layer, the suture was disinfected with alcohol. After SD rats woke up, the rats were put into a cage for feeding. In the blank group, ureter was not ligated, and other steps were the same.

Then, the animals fell into a blank group, a model group, and recombinant fused polypeptide administration groups, and the administration was started on the second day after the operation, and was performed for 15 days. After administration for 15 days, blood was taken and supernatant was taken to detect the content of TGF-$\beta$1 in serum.

4. Experimental Grouping and Dosage Setting

TABLE 4

Experimental grouping and dosage regimen

| Group | Drug | Dosage | Administration mode | Administration frequency | Quantity |
|---|---|---|---|---|---|
| Blank group | Normal saline | 0.5 mL/200 g | Subcutaneous injection | Once a day | 10 |
| Model group | Normal saline | 0.5 mL/200 g | Subcutaneous injection | Once a day | 10 |
| Test drug (1) | Fused polypeptide 1 | 6 mg/kg | Subcutaneous injection | Once every five days | 10 |
| Test drug (2) | Fused polypeptide 2 | 6 mg/kg | Subcutaneous injection | Once every five days | 10 |

TABLE 4-continued

Experimental grouping and dosage regimen

| Group | Drug | Dosage | Administration mode | Administration frequency | Quantity |
|---|---|---|---|---|---|
| Test drug (3) | Fused polypeptide 3 | 6 mg/kg | Subcutaneous injection | Once every five days | 10 |
| Test drug (4) | Fused polypeptide 4 | 6 mg/kg | Subcutaneous injection | Once every five days | 10 |

Figure 4:
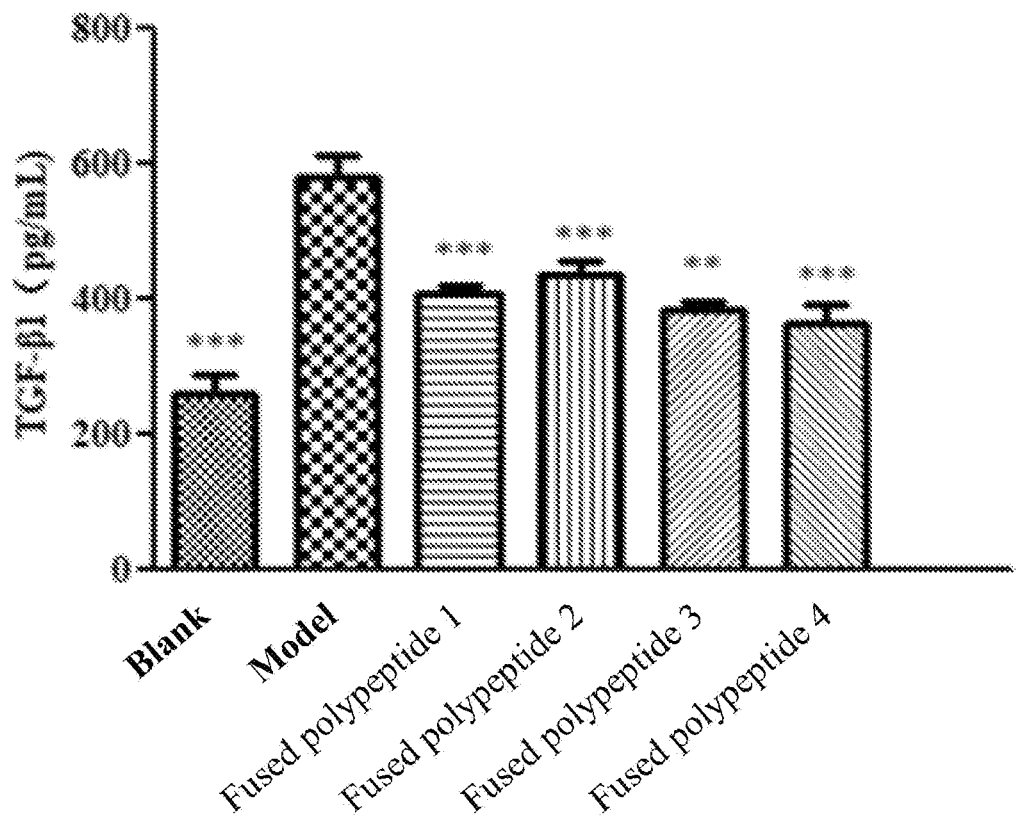
FIG. 4 is a diagram showing that recombinant fused polypeptides I, II, III and IV according to the present invention can lower the TGF-β1 content in a renal fibrosis model.

5. Experimental Results (1) Impact of a Recombinant Fused Polypeptide on the Content of TGF-β1 in Serum of SD Rats with Renal Fibrosis TGF-β1 is the most important fibrogenic factor. In renal fibrosis, the expression of TGF-β1 was significantly increased. The result is shown in FIG. 4, and there was a highly significant difference between the model group and the blank group (*P<0.001). After administration, all groups could significantly reduce the content of TGF-β1 in serum, and the recombinant fused polypeptide 1 group, the recombinant fused polypeptide 2 group and the recombinant fused polypeptide 4 group were highly significantly different from the model group (*P<0.001), and the recombinant fused polypeptide 3 group was highly significantly different from the model group (**P<0.01).

Example 5 Myocardial Fibrosis Animal Model

1. Experimental Mice: 10-Week-Old Male BALB/c Mice (with an Average Weight of 20 g).
2. Experimental Materials:

| Normal saline | Manufacturer: Anhui Double-Crane Pharmaceutical Co., Ltd. |
| Rat TGF-β1 ELISA kit | Manufacturer: Tianjin Annuo Ruikang Biotechnology Co., Ltd. |
| Isoprenaline (ISO) | Manufacturer: Sigma |

3. Experimental Method

In the model group, the experimental mice were injected with isoprenaline (ISO) (5 mg/kg) subcutaneously on the back of the mice every day for 7 consecutive days, and the mice were injected with normal saline subcutaneously (200 μL/mouse) every day. In the blank group, normal saline was injected subcutaneously (200 μL/mouse) every day. While a model was made, recombinant fused polypeptide drugs were administrated for treatment twice a day by subcutaneous injection. After the 8$^{th}$ day, blood was taken and was centrifuged, the supernatant was taken, and the content of TGF-β1 in serum was detected.

4. Experimental Grouping and Dosage Setting

TABLE 5

Experimental grouping and dosage regimen

| Group | Drug | Dosage | Administration mode | Administration frequency | Quantity |
|---|---|---|---|---|---|
| Blank group | Normal saline | 0.2 mL | Subcutaneous injection | Once a day | 10 |
| Model group | Normal saline | 0.2 mL | Subcutaneous injection | Once a day | 10 |
| Test drug (1) | Fused polypeptide 1 | 12 mg/kg | Subcutaneous injection | Once every five days | 10 |
| Test drug (2) | Fused polypeptide 2 | 12 mg/kg | Subcutaneous injection | Once every five days | 10 |
| Test drug (3) | Fused polypeptide 3 | 12 mg/kg | Subcutaneous injection | Once every five days | 10 |
| Test drug (4) | Fused polypeptide 4 | 12 mg/kg | Subcutaneous injection | Once every five days | 10 |

Figure 5:
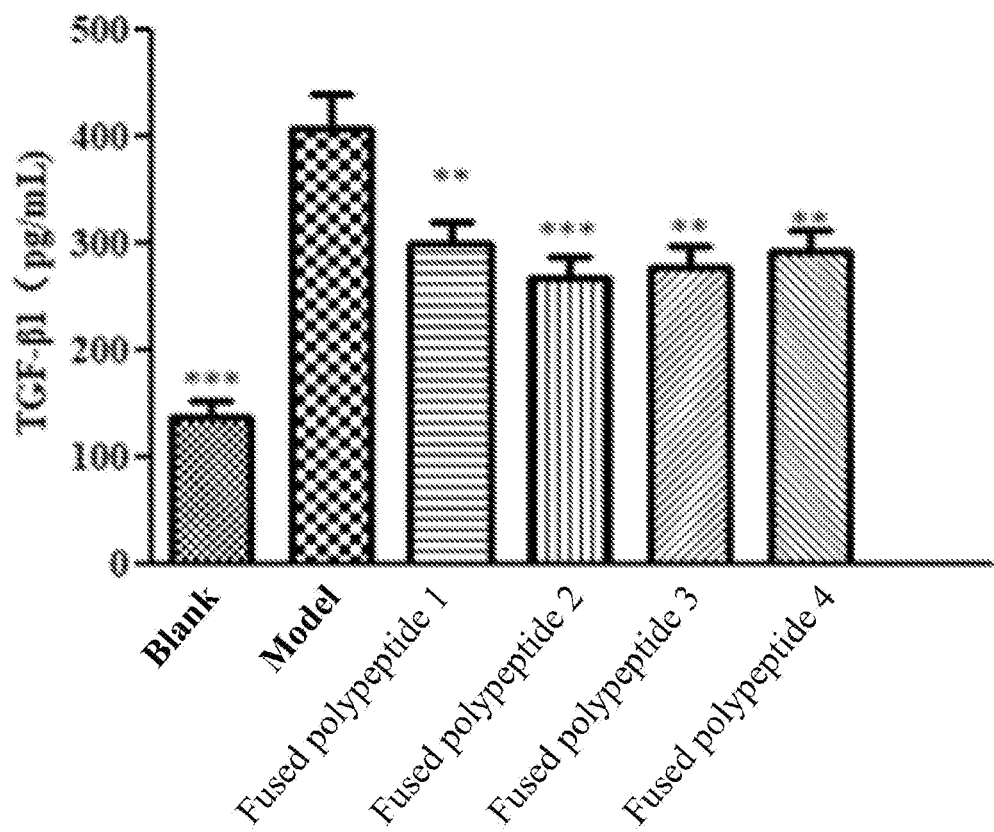
FIG. 5 is a diagram showing that recombinant fused polypeptides I, II, III and IV according to the present invention can lower the TGF-β1 content in a myocardial fibrosis model.

5. Experimental Results (1) Impact of a recombinant fused polypeptide on the content of TGF-β1 in serum of mice with myocardial fibrosis TGF-β1 is the most important fibrogenic factor. In myocardial fibrosis, the expression of TGF-131 was significantly increased. The result is shown in FIG. 5, and there was a highly significant difference between the model group and the blank group (*P<0.001). After administration, all groups could significantly reduce the content of TGF-β1 in serum, the recombinant fused polypeptide 2 group was highly significantly different from the model group (*P<0.001), and the recombinant fused polypeptide 1 group, the recombinant fused polypeptide 3 group and the recombinant fused polypeptide 4 group were significantly different from the model group (**P<0.01).

Example 6 Establishment of a Skin Fibrosis Model

1. Experimental Animals

Male C57/BL Black Mice Aged 6-8 Weeks, Purchased from Nanjing Qinglong Mountain Animal Farm.

2. Experimental Materials

| Bleomycin | Manufacturer: Han Hui Pharmaceutical Co., Ltd. |
| Normal saline | Manufacturer: Anhui Double-Crane Pharmaceutical Co., Ltd. |
| Rat TGF-β1 ELISA kit | Manufacturer: Tianjin Annuo Ruikang Biotechnology Co., Ltd. |
| Alkaline HYP kit | Manufacturer: Nanjing Jiancheng Bioengineering Institute |

3. Modeling Method

Bleomycin (10 μg/mL) was injected subcutaneously every day for 28 days to form skin fibrosis. During the modeling period, the administration groups were given drugs for treatment. After modeling, the mice were killed on the next day, and the skin tissue of the mouse back was taken to detect the content of HYP in the skin tissue.

4. Experimental Grouping and Dosage Regimen

TABLE 6

Experimental grouping and dosage regimen

| Group | Drug | Dosage | Administration mode | Administration frequency | Times of administration |
|---|---|---|---|---|---|
| Blank group | Normal saline | 0.2 mL | Subcutaneous injection | Once every five days | 6 times |
| Model group | Normal saline | 0.2 mL | Subcutaneous injection | Once every five days | 6 times |
| Test drug (1) | Fused polypeptide 1 | 10 mg/kg | Subcutaneous injection | Once every five days | 6 times |
| Test drug (2) | Fused polypeptide 2 | 10 mg/kg | Subcutaneous injection | Once every five days | 6 times |
| Test drug (3) | Fused polypeptide 3 | 10 mg/kg | Subcutaneous injection | Once every five days | 6 times |
| Test drug (4) | Fused polypeptide 4 | 10 mg/kg | Subcutaneous injection | Once every five days | 6 times |

Figure 6:
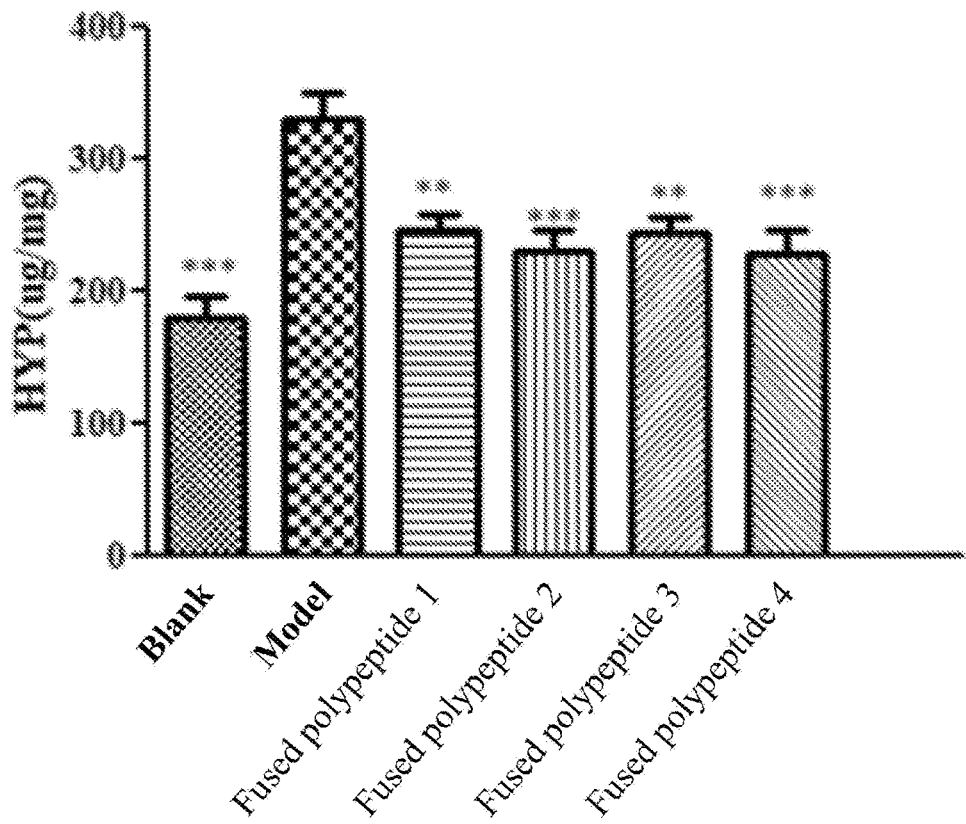
FIG. 6 is a diagram showing that recombinant fused polypeptides I, II, III and IV according to the present invention can lower the hydroxyproline content in a skin fibrosis model.

1. Experimental Results (1) Expression of HYP Content in the Skin Tissue of Each Group of Mice The content of hydroxyproline in the skin tissue of the mouse back was detected to obtain the results shown in FIG. 6. As the characteristic protein of collagen, hydroxyproline can reflect the content of collagen in the skin tissue from the side. As shown in FIG. 6, each recombinant fused polypeptide group could reduce the expression of HYP in the skin tissue. The recombinant fused polypeptide 2 group and the recombinant fused polypeptide 4 group could significantly reduce the expression of HYP in the lung tissue, and were highly significantly different from the model group (*$P<0.001$). The recombinant fused polypeptide 1 group and the recombinant fused polypeptide 3 group could reduce the content of HYP in the lung tissue of SD rats, and were highly significantly different from the model group ($P<0.01$).

Figure 7:
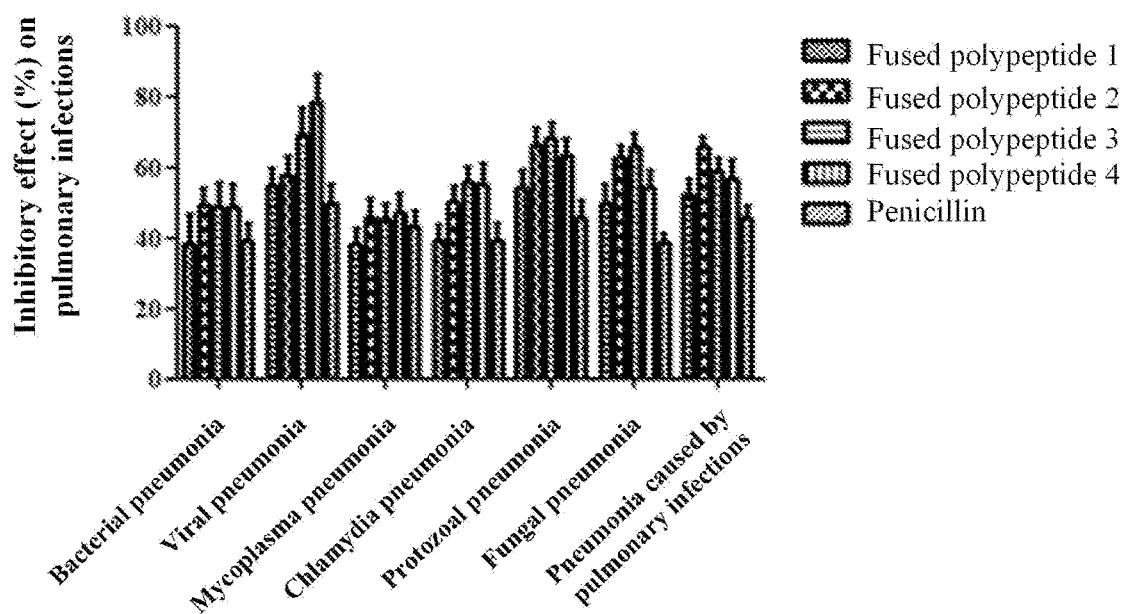
FIG. 7 shows an inhibitory effect of recombinant fused polypeptides I, II III and IV according to the present invention on pulmonary infections.

Example 7 Inhibitory Effect of a Recombinant Fused Polypeptide According to the Present Invention on Multiple Pulmonary Infections A mouse pneumonia model was successfully established by using a nasal drip method. BALB/C mice with a body weight of 18-24 g were selected, and then anesthetized with ether on day 0, day 1 and day 2, respectively, prepared *Streptococcus pneumoniae* bacteria solution, adenovirus concentrated solution, *Mycoplasma pneumoniae*, *Chlamydia pneumoniae*, protozoa and pneumonia fungi were slowly dropped into the nasal cavity of the mice, so that the bacteria solutions entered the trachea and bronchi, and the bacteria solutions were prevented from flowing into the esophagus during the operation to avoid inactivation of the bacteria solutions, so that the mouse pneumonia model was established. After the model was successfully established, the recombinant fused polypeptides according to the present invention were administered. The results in Table 7 show that compared with the drug in the penicillin administration group, the recombinant fused polypeptides according to the present invention had a more significant improvement effect on a plurality of lung infections. The experimental results are represented on the basis of average values±standard deviation, as shown in FIG. 7.

TABLE 7

Inhibitory effect of a recombinant fused polypeptide according to the present invention on multiple pulmonary infections

| Pneumonia type | Fused polypeptide 1 | Fused polypeptide 2 | Fused polypeptide 3 | Fused polypeptide 4 | Penicillin |
|---|---|---|---|---|---|
| Bacterial pneumonia | 38.43 ± 8.25 | 49.18 ± 5.32 | 48.79 ± 7.26 | 48.61 ± 6.54 | 39.21 ± 5.35 |
| Viral pneumonia | 54.68 ± 5.23 | 58.08 ± 5.27 | 69.54 ± 7.49 | 78.12 ± 8.27 | 50.07 ± 5.12 |
| Mycoplasma pneumonia | 38.47 ± 4.35 | 45.72 ± 5.69 | 45.53 ± 4.33 | 47.30 ± 5.30 | 43.21 ± 4.56 |
| Chlamydia pneumonia | 39.26 ± 4.66 | 50.21 ± 4.85 | 55.78 ± 4.32 | 55.26 ± 6.12 | 39.13 ± 5.23 |
| Protozoal pneumonia | 54.26 ± 5.32 | 66.13 ± 5.36 | 68.29 ± 4.70 | 63.45 ± 4.68 | 45.62 ± 5.43 |
| Fungal pneumonia | 49.68 ± 5.74 | 63.07 ± 3.02 | 65.98 ± 3.64 | 54.12 ± 5.12 | 38.89 ± 2.24 |
| Pneumonia caused by pulmonary infections | 52.47 ± 4.28 | 65.87 ± 3.19 | 58.81 ± 4.10 | 56.93 ± 5.28 | 45.78 ± 3.65 |

What is claimed is:

1. A recombinant fused polypeptide, wherein the recombinant fused polypeptide comprises a polypeptide X and a polypeptide Y, which are expressed by the following general formula: X-linker1-Y; Y-linker1-X; X-linker2-Y; Y-linker2-X, wherein X is PRCWRGEGGGGIVRRADRAAVPGGG-GRGD (SEQ ID NO: 5); and Y is SDKPGGGGTSLDASII-WAMMQNGGGGLSKL (SEQ ID NO: 6).

2. The recombinant fused polypeptide according to claim 1, wherein linker1 is GGGGSGGGGSGGGGS (SEQ ID NO: 7); and linker2 is AEAAAKEAAAKEAAAKEAAAKK (SEQ ID NO: 8).

3. The recombinant fused polypeptide according to claim 1, wherein an amino acid sequence of the fused polypeptide is any one of the following:

(SEQ ID NO: 1)
PRCWRGEGGGGIVRRADRAAVPGGGGRGDGGGGSGGGGSG

GGGSSDKPGGGGTSLDASIIWAMMQNGGGGLSKL;

(SEQ ID NO: 2)
SDKPGGGGTSLDASIIWAMMQNGGGGLSKLGGGGSGGGGS

GGGGSPRCWRGEGGGGIVRRADRAAVPGGGGRGD;

(SEQ ID NO: 3)
PRCWRGEGGGGIVRRADRAAVPGGGGRGDAEAAAKEAAAK

EAAAKEAAAKKSDKPGGGGTSLDASIIWAMMQNGGGGLSK

L;

and (SEQ ID NO: 4)
SDKPGGGGTSLDASIIWAMMQNGGGGLSKLAEAAAKEAAA

KEAAAKEAAAKKPRCWRGEGGGGIVRRADRAAVPGGGGRG

D.

4. A recombinant fused polypeptide, wherein the polypeptide comprises a polypeptide sequence with 80% homology with the amino acid sequence of the fused polypeptide according to claim 1.

5. A method for the preparation of anti-fibrosis drugs, comprising providing a pharmaceutical composition comprising the recombinant fused polypeptide of claim 1.

6. The method of claim 5, wherein the anti-fibrosis drug is used to treat a tissue fibrosis selected from the group consisting of pulmonary fibrosis, hepatic fibrosis, renal fibrosis, myocardial fibrosis, and skin fibrosis, wherein the treating comprises administering the pharmaceutical composition of claim 5 to a subject in need thereof.

7. The method of claim 6, wherein the tissue fibrosis comprises lung tissue lesions comprising bacterial pneumonia, viral pneumonia, mycoplasma pneumonia, fungal pneumonia, chlamydia pneumonia or protozoal pneumonia.

8. The method of claim 5, wherein the pharmaceutical composition is administered in an injection, a capsule, a tablet, a nasal spray or an aerosol.

9. The method of claim 7, wherein the pharmaceutical composition is administered to treat lung lesions and is in the form of an injection, a capsule, a tablet, a nasal spray or an aerosol.

* * * * *

SEQUENCE LISTING

<160> NUMBER OF SEQ ID NOS: 8

<210> SEQ ID NO 1
<211> LENGTH: 74
<212> TYPE: PRT
<213> ORGANISM: Artificial Sequence
<220> FEATURE:
<223> OTHER INFORMATION: synthesized

<400> SEQUENCE: 1

Pro Arg Cys Trp Arg Gly Glu Gly Gly Gly Ile Val Arg Arg Ala
1               5                   10                  15

Asp Arg Ala Ala Val Pro Gly Gly Gly Arg Gly Asp Gly Gly Gly
                20                  25                  30

Gly Ser Gly Gly Gly Ser Gly Gly Gly Ser Ser Asp Lys Pro
            35                  40                  45

Gly Gly Gly Gly Thr Ser Leu Asp Ala Ser Ile Ile Trp Ala Met Met
    50                  55                  60

Gln Asn Gly Gly Gly Gly Leu Ser Lys Leu
65                  70

<210> SEQ ID NO 2
<211> LENGTH: 74
<212> TYPE: PRT
<213> ORGANISM: Artificial Sequence
<220> FEATURE:
<223> OTHER INFORMATION: synthesized

<400> SEQUENCE: 2

Ser Asp Lys Pro Gly Gly Gly Gly Thr Ser Leu Asp Ala Ser Ile Ile
1               5                   10                  15

Trp Ala Met Met Gln Asn Gly Gly Gly Leu Ser Lys Leu Gly Gly
                20                  25                  30

Gly Gly Ser Gly Gly Gly Ser Gly Gly Gly Ser Pro Arg Cys
            35                  40                  45

Trp Arg Gly Glu Gly Gly Gly Ile Val Arg Arg Ala Asp Arg Ala
    50                  55                  60

Ala Val Pro Gly Gly Gly Gly Arg Gly Asp
65                  70

<210> SEQ ID NO 3
<211> LENGTH: 81
<212> TYPE: PRT
<213> ORGANISM: Artificial Sequence
<220> FEATURE:
<223> OTHER INFORMATION: synthesized

<400> SEQUENCE: 3

Pro Arg Cys Trp Arg Gly Glu Gly Gly Gly Ile Val Arg Arg Ala
1               5                   10                  15

Asp Arg Ala Ala Val Pro Gly Gly Gly Arg Gly Asp Ala Glu Ala
                20                  25                  30

Ala Ala Lys Glu Ala Ala Ala Lys Glu Ala Ala Ala Lys Glu Ala Ala
            35                  40                  45

Ala Lys Lys Ser Asp Lys Pro Gly Gly Gly Gly Thr Ser Leu Asp Ala
    50                  55                  60

Ser Ile Ile Trp Ala Met Met Gln Asn Gly Gly Gly Gly Leu Ser Lys
65                  70                  75                  80

Leu

<210> SEQ ID NO 4
<211> LENGTH: 81
<212> TYPE: PRT
<213> ORGANISM: Artificial Sequence
<220> FEATURE:
<223> OTHER INFORMATION: synthesized

<400> SEQUENCE: 4

```
Ser Asp Lys Pro Gly Gly Gly Thr Ser Leu Asp Ala Ser Ile Ile
1               5                   10                  15

Trp Ala Met Met Gln Asn Gly Gly Gly Leu Ser Lys Leu Ala Glu
                20                  25                  30

Ala Ala Ala Lys Glu Ala Ala Lys Glu Ala Ala Lys Glu Ala
            35                  40                  45

Ala Ala Lys Lys Pro Arg Cys Trp Arg Gly Glu Gly Gly Gly Ile
        50                  55                  60

Val Arg Arg Ala Asp Arg Ala Ala Val Pro Gly Gly Gly Arg Gly
65                  70                  75                  80

Asp
```

<210> SEQ ID NO 5
<211> LENGTH: 29
<212> TYPE: PRT
<213> ORGANISM: Artificial Sequence
<220> FEATURE:
<223> OTHER INFORMATION: synthesized

<400> SEQUENCE: 5

```
Pro Arg Cys Trp Arg Gly Glu Gly Gly Gly Ile Val Arg Arg Ala
1               5                   10                  15

Asp Arg Ala Ala Val Pro Gly Gly Gly Gly Arg Gly Asp
                20                  25
```

<210> SEQ ID NO 6
<211> LENGTH: 30
<212> TYPE: PRT
<213> ORGANISM: Artificial Sequence
<220> FEATURE:
<223> OTHER INFORMATION: synthesized

<400> SEQUENCE: 6

```
Ser Asp Lys Pro Gly Gly Gly Gly Thr Ser Leu Asp Ala Ser Ile Ile
1               5                   10                  15

Trp Ala Met Met Gln Asn Gly Gly Gly Gly Leu Ser Lys Leu
                20                  25                  30
```

<210> SEQ ID NO 7
<211> LENGTH: 15
<212> TYPE: PRT
<213> ORGANISM: Artificial Sequence
<220> FEATURE:
<223> OTHER INFORMATION: synthesized

<400> SEQUENCE: 7

```
Gly Gly Gly Gly Ser Gly Gly Gly Gly Ser Gly Gly Gly Gly Ser
1               5                   10                  15
```

<210> SEQ ID NO 8
<211> LENGTH: 22
<212> TYPE: PRT
<213> ORGANISM: Artificial Sequence
<220> FEATURE:
<223> OTHER INFORMATION: synthesized

```
<400> SEQUENCE: 8

Ala Glu Ala Ala Ala Lys Glu Ala Ala Ala Lys Glu Ala Ala Ala Lys
1               5                   10                  15

Glu Ala Ala Ala Lys Lys
            20
```